US00PP27230P3

(12) United States Plant Patent
Schoone

(10) Patent No.: US PP27,230 P3
(45) Date of Patent: Oct. 4, 2016

(54) ***PHALAENOPSIS* ORCHID PLANT NAMED 'PENNY LANE'**

(50) Latin Name: *Phalaenopsis hybrida*
Varietal Denomination: Penny Lane

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 0 days.

(21) Appl. No.: 14/545,313

(22) Filed: Apr. 22, 2015

(65) Prior Publication Data

US 2015/0313062 P1 Oct. 29, 2015

Related U.S. Application Data

(60) Provisional application No. 61/984,230, filed on Apr. 25, 2014.

(30) Foreign Application Priority Data

Apr. 29, 2014 (NL) ..... PBR OPS1116

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Jun. 11, 2016. p. 1.*

* cited by examiner

*Primary Examiner* — Annette Para
(74) *Attorney, Agent, or Firm* — Foley & Lardner LLP; Sunit Talapatra

(57) ABSTRACT

A new and distinct *Phalaenopsis* plant named 'Penny Lane' particularly characterized by flowers which are yellow with red/purple spots and stripes; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Penny Lane'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Penny Lane'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Penny Lane' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Penny Lane' originated from a cross made by the inventor in 2001 in Strengweg, Heemskerk, The Netherlands. The female or seed parent is the *Phalaenopsis* cultivar designated 'Sunrise Delight', unpatented. The male or pollen parent is the *Phalaenopsis* cultivar designated 'Timothy Christopher', unpatented. The new *Phalaenopsis* 'Penny Lane' was discovered and selected by the inventor as a single flowering plant within the progeny of the stated cross in a controlled environment in 2009 in Strengweg, Heemskerk, The Netherlands.

Asexual reproduction of the new *Phalaenopsis* cultivar by tissue culture (mericloning) was first performed in November, 2009 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true-to-type.

BRIEF DESCRIPTION OF THE INVENTION

The following traits have been repeatedly observed and are determined to be unique characteristics of 'Penny Lane', which in combination distinguish this *Phalaenopsis* as a new and distinct cultivar:

1. flowers which are yellow with red/purple spots and stripes;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Penny Lane', the female parent 'Sunrise Delight' is yellow/orange with darker stripes and pink in the labellum, the male parent 'Timothy Christopher' is white with little yellow in labellum, whereas the flowers of 'Penny Lane' are yellow with red/purple spots and stripes and a red/purple labellum.

Presently, the commercial cultivar to which 'Penny Lane' can be meaningfully compared is 'Midsummer' (unpatented). The raceme and the flowers of 'Midsummer' are a little larger and the labellum and the spots/stripes of 'Midsummer' are purple, whereas the labellum and the spots/stripes of 'Penny Lane' are more red/purple.

BRIEF DESCRIPTION OF THE PHOTOGRAPHS

The accompanying photographs illustrate the overall appearance of the new *Phalaenopsis* 'Penny Lane' showing the colors as true as is reasonably possible with colored reproductions of this type. Colors in the photographs may differ slightly from the color values cited in the detailed botanical description, which accurately describe the color of 'Penny Lane'.

DETAILED BOTANICAL DESCRIPTION

Figure 1:
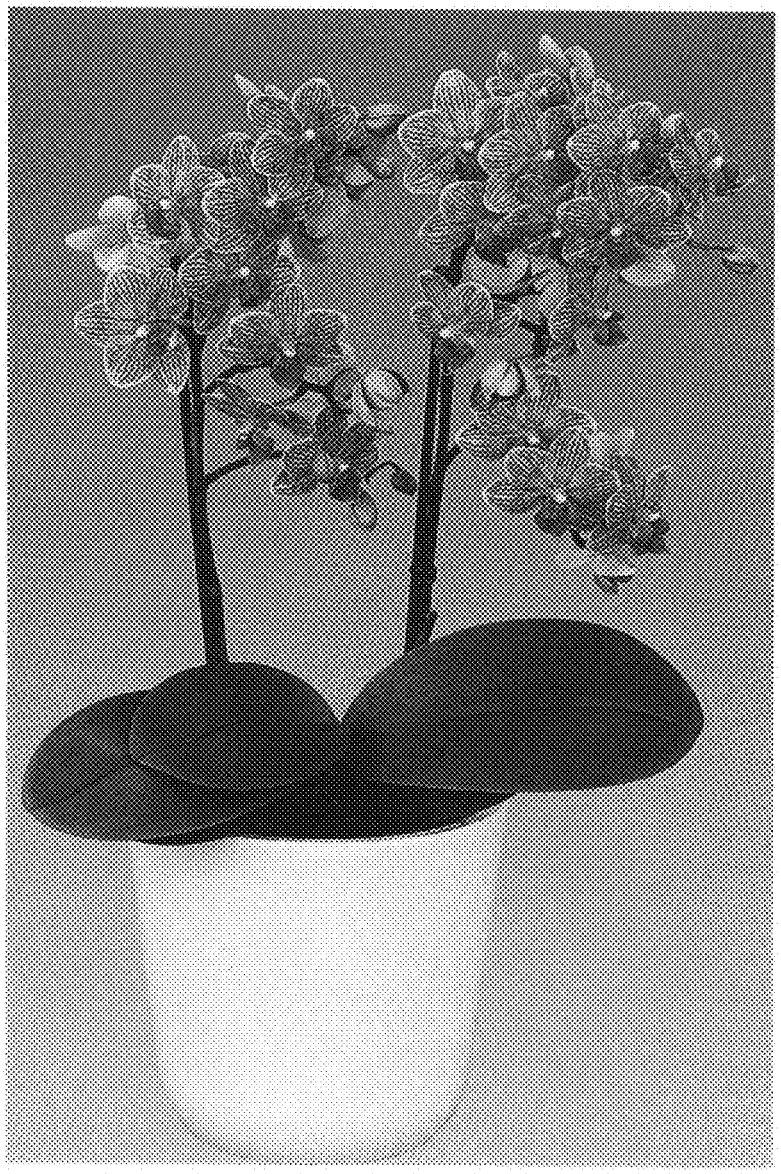
FIG. 1 shows a side view perspective of a typical flowering plant of 'Penny Lane' in a 12 cm pot, at 16 months of age.

The new *Phalaenopsis* cultivar 'Penny Lane' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Penny Lane' as grown in a greenhouse in Strengweg, Heemskerk, The Netherlands, under conditions which closely approximate those generally used in commercial practice. Initially, the ideal temperature to grow plants of 'Penny Lane' is 27° C. during the day and at night. Then, during the flowering phase of 'Penny Lane', the ideal growing temperature is 20-22° C. during the day and 18° C. at night. Light levels for growing 'Penny Lane' are a minimum of 5,000 lux and a maximum of 10,000 lux. A balanced fertilizer with level of 200 ppm N, 87 ppm P, 168 ppm K is applied. Duration of growth of 'Penny Lane' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Penny Lane' plants described is 12 months after potting.

Classification:

*Botanical.—Phalaenopsis hybrida.*

Parentage:

*Female or seed parent.—Phalaenopsis* cultivar designated 'Sunrise Delight', unpatented.

*Male or pollen parent.—Phalaenopsis* cultivar designated 'Timothy Christopher, unpatented.

Propagation:

*Type.*—Tissue culture.

*Rooting habit and description.*—Fleshy; approximately 3 mm-5 mm wide and greyed/green in color (RHS 190A); freely branching. It takes 12 weeks for plants growing in tissue culture to initiate roots.

Plant:

*Size at maturity.*—Height (from bottom of pot to highest flower): about 45 cm. Spread: about 25 cm.

*Growth habit.*—Small; green leaves (RHS 137C) and a relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1-2 racemes with flowers appear.

Foliage:

*Quantity per plant.*—About 6-8 leaves are produced before flowering.

*Arrangement and attachment.*—Half up/horizontal and on two sides.

*Overall shape of leaf.*—Oval; the tip is blunt and asymmetric.

*Texture (upper & underside).*—Smooth and leathery.

*Pubescence.*—None.

*Mature leaf length.*—About 13 cm.

*Mature leaf width.*—About 7 cm.

*Mature leaf thickness.*—About 2 mm.

*Mature leaf color.*—Upper side: green (RHS 137C). Under side: yellow/green (RHS 138A).

*Leaf base.*—Acute.

*Margin.*—Entire.

*Venation.*—Pattern: parallel. Color of midvein: upper side: green (RHS 137A) under side: green (RHS 137C).

Inflorescence description:

*Appearance.*—Upright to slightly pendant, racemose inflorescence with bilaterally symmetrical flowers that open in succession beginning with the lowermost flower.

*Raceme.*—Quantity per plant: about 1 to 2. Number of flowers per raceme: about 15-30. Length: about 35 cm.

*Peduncle.*—Diameter: about 4 mm. Strength: strong. Aspect: upright. Texture: glabrous and smooth. Color: green (RHS N137A) with brown (RHS 200A). Internode: Length: about 25 mm.

*Buds*.—Height (from base to tip): about 17 mm. Diameter (at midpoint): about 13 mm. Shape: oval/egg-shaped with a bump on one side. Color: yellow/green (RHS 145A) with a red/purple haze (RHS 59A).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1-2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
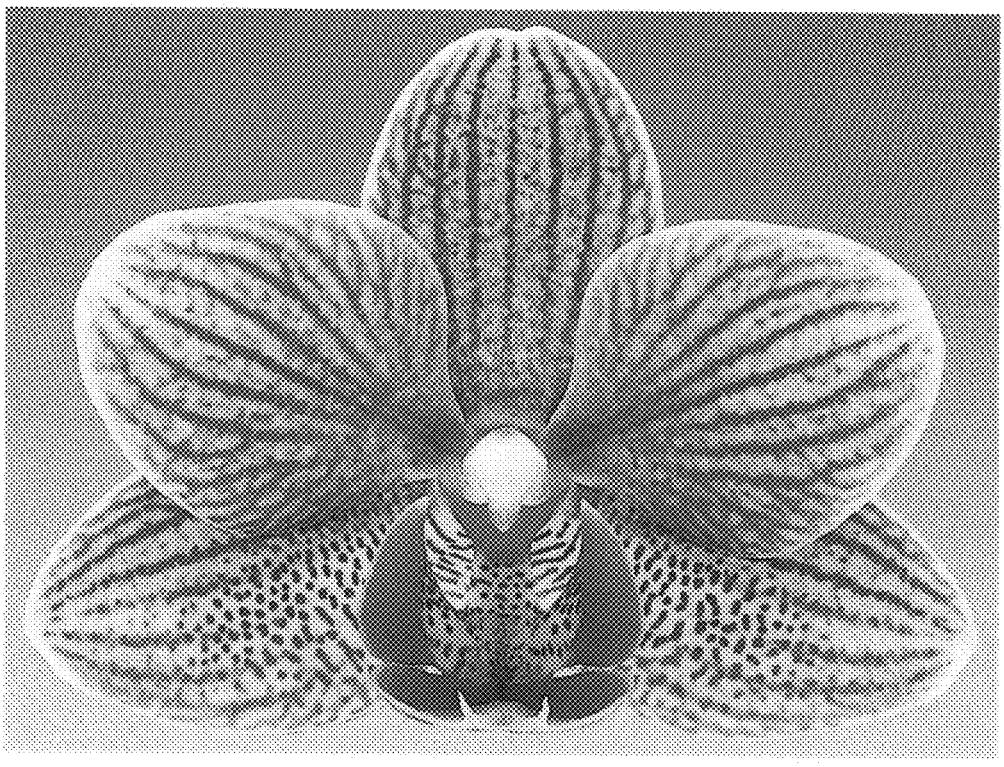
FIG. 2 shows a close-up view of the typical flower of 'Penny Lane'.
Figure 3:
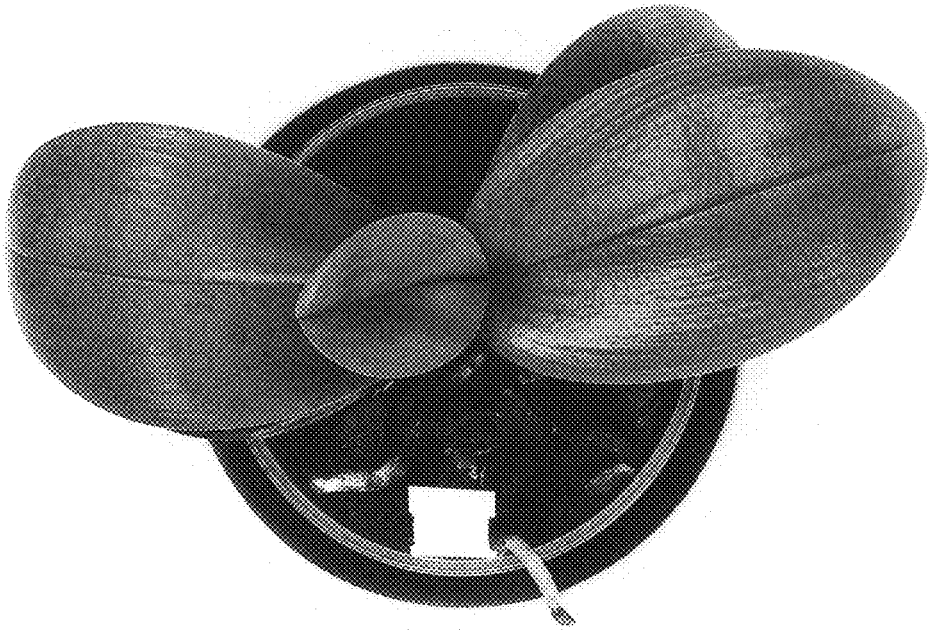
FIG. 3 shows a close-up view of the typical leaves of 'Penny Lane'.

*Flower*.—Rate of opening: Flowers fully opened about 2 to 3 days after petal and sepal separation. Orientation at opening: slanted upward and outward. Shape: Typical shape of *Phalaenopsis*, see FIG. 2. Size (of single bloom): Height: about 43 mm. Diameter: about 48 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and a labellum. 2 lateral petals: Overall shape: broadly ovate and weakly cupped. Apex: oval/round. Margin: entire and weakly undulate. Base: broadly ovate. Length: about 20 mm. Width: about 22 mm. Texture: Upper surface: smooth and satiny. Under surface: smooth and satiny. Color (when fully opened): upper side: yellow (RHS 3C) with red/purple spots/stripes (RHS 71A) and a red/purple haze (RHS 71A). Under side: yellow (RHS 4C) with at the sides some red/purple (RHS 71A). Labellum: Overall shape: 3-lobed with 2 prominent callosities at central junction of the lateral lobes and base of the midlobe. Lateral lobes of labellum fold upward about the column; the midlobe extends forward and is terminated by 2 stubs appendages at the apex. Lateral lobes of the labellum are ovate in shape while the midlobe is triangular with a bump and a rib on it. Margin: entire and weakly undulate. Apex: oval. Length: about 21 mm. Width (not flattened): about 15 mm. Depth of tube created by lateral lobes of labellum: about 7 mm. Texture: Upper & under surface: smooth and satiny. Color (when fully opened): Mid lobe, upper side: main color is red/purple (RHS 60B) with some red/purple stripes/spots (RHS 72A and RHS 59B). The edges are yellow/orange (RHS 14A) and part of the vein is red/purple (RHS 59A). Under side: At the base some yellow (RHS 4A) which runs into white (RHS NN155B) and red/purple on the sides (RHS 59B). Lateral lobes, upper side: main color is red/purple (RHS 60B) with some red/purple (RHS 59A) stripes and spots. At the base and on the sides some yellow (RHS 13A). Under side: yellow/green (RHS 1D) with red/purple spots (RHS 59B and RHS 60B). Cirrhi: about 4 mm. Color: red/purple (RHS 59B) with yellow (RHS 4A). Pestle (Callosities): Length: about 3 mm. Width (not flattened): about 3 mm. Color: yellow (RHS 13A) with red/purple spots (RHS 59A).

*Sepals*.—Arrangement: Outer whorl comprises 3 sepals, one dorsal and two lateral sepals. Overall shape: elliptical and weakly cupped. Margin: entire and weakly undulate. Length: about 24 mm. Width: about 17 mm. Apex: oval and little pointy. Texture: Upper and under surface: smooth and satiny. Color (when fully opened): Upper side: Dorsal: yellow (RHS 13D) with red/purple spots and stripes (RHS 71A) and a red/purple haze (RHS 71A). Lateral: yellow (RHS 13D) with a yellow/green haze (RHS 145B) and red/purple spots/stripes a red/purple haze (RHS 71A). Under side: Dorsal & lateral: main color is yellow/green (RHS 145C) with on de side a red/purple haze (RHS 71A).

*Pedicel*.—Length: about 25 mm. Diameter: about 3 mm. Texture: glabrous and smooth. Color: green/white (RHS 157B) with red/purple haze (RHS 70A) which runs into yellow/green (RHS 145A).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 10 mm. Diameter: about 3 mm. Color: white (RHS NN155D) with red/purple (RHS 72B).

*Pollinia*.—Quantity: two. Diameter: about 2 mm. Color: yellow/orange (RHS 17A).

*Ovary*.—Length: about 2 mm. Diameter: about 2 mm. Color: white (RHS NN155D).

Disease/pest resistance/ susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Penny Lane', as illustrated and described herein.

* * * * *